United States Patent
Bawiec, III et al.

(10) Patent No.: US 9,029,604 B2
(45) Date of Patent: May 12, 2015

(54) LOW MOLECULAR WEIGHT CATIONIC LIPIDS FOR OLIGONUCLEOTIDE DELIVERY

(75) Inventors: John A. Bawiec, III, Wilkes-Barre, PA (US); Zhengwu J. Deng, Eagleville, PA (US)

(73) Assignee: Sirna Therapeutics, Inc., Cambridge, MA (US)

( * ) Notice: Subject to any disclaimer, the term of this patent is extended or adjusted under 35 U.S.C. 154(b) by 0 days.

(21) Appl. No.: 13/876,528

(22) PCT Filed: Sep. 28, 2011

(86) PCT No.: PCT/US2011/053556
§ 371 (c)(1),
(2), (4) Date: Mar. 28, 2013

(87) PCT Pub. No.: WO2012/044638
PCT Pub. Date: Apr. 5, 2012

(65) Prior Publication Data
US 2013/0274523 A1    Oct. 17, 2013

Related U.S. Application Data

(60) Provisional application No. 61/388,201, filed on Sep. 30, 2010.

(51) Int. Cl.
| | | |
|---|---|---|
| C07C 217/46 | (2006.01) | |
| C12N 15/88 | (2006.01) | |
| C07C 217/08 | (2006.01) | |
| A61K 9/51 | (2006.01) | |

(52) U.S. Cl.
CPC ............ *C07C 217/08* (2013.01); *A61K 9/5123* (2013.01); *C12N 15/88* (2013.01); *C07C 2101/02* (2013.01); *Y10S 977/783* (2013.01); *Y10S 977/916* (2013.01)

(58) Field of Classification Search
None
See application file for complete search history.

(56) References Cited

U.S. PATENT DOCUMENTS

| | | |
|---|---|---|
| 5,614,548 A | 3/1997 | Piantadosi et al. |
| 2006/0083780 A1 | 4/2006 | Heyes et al. |
| 2006/0240554 A1 | 10/2006 | Chen et al. |
| 2008/0020058 A1 | 1/2008 | Chen et al. |
| 2008/0188675 A1 | 8/2008 | Chen et al. |
| 2009/0263407 A1 | 10/2009 | Dande et al. |
| 2009/0285881 A1 | 11/2009 | Dande et al. |
| 2010/0055168 A1 | 3/2010 | Dande et al. |
| 2010/0055169 A1 | 3/2010 | Dande et al. |
| 2010/0063135 A1 | 3/2010 | Dande et al. |
| 2010/0076055 A1 | 3/2010 | Dande et al. |
| 2010/0099738 A1 | 4/2010 | Hansen et al. |
| 2010/0104629 A1 | 4/2010 | Dande et al. |

FOREIGN PATENT DOCUMENTS

| | | |
|---|---|---|
| WO | WO2009/086558 A1 | 7/2009 |
| WO | WO2009/127060 A1 | 10/2009 |
| WO | WO2009/132131 A1 | 10/2009 |
| WO | WO2010/042877 A1 | 4/2010 |
| WO | WO2010/054384 A1 | 5/2010 |
| WO | WO2010/054401 A1 | 5/2010 |
| WO | WO2010/054405 A1 | 5/2010 |
| WO | WO2010/054406 A1 | 5/2010 |

OTHER PUBLICATIONS

Database CAPLUS on STN, Acc. No. 2004:252471, Tendo et al., WO 2004024672 Al (Mar. 25, 2004) (abstract).*
Database CAPLUS on STN, Acc. No. 2000:13143, Chiou et al., Organic Letters (2000), 2(3), pp. 347-350 (abstract).*

* cited by examiner

*Primary Examiner* — Brian J Davis
(74) *Attorney, Agent, or Firm* — Nixon Peabody LLP

(57) ABSTRACT

The instant invention provides for novel cationic lipids that can be used in combination with other lipid components such as cholesterol and PEG-lipids to form lipid nanoparticles with oligonucleotides. It is an object of the instant invention to provide a cationic lipid scaffold that demonstrates enhanced efficacy along with lower liver toxicity as a result of lower lipid levels in the liver. The present invention employs low molecular weight cationic lipids with one short lipid chain to enhance the efficiency and tolerability of in vivo delivery of siRNA.

11 Claims, 2 Drawing Sheets

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified or unmodified as
      described for this sequence
<220> FEATURE:
<221> NAME/KEY: misc_feature
<222> LOCATION: (1)..(1)
<223> OTHER INFORMATION: inverted deoxy abasic
<220> FEATURE:
<221> NAME/KEY: misc_feature
<222> LOCATION: (1)..(1)
<223> OTHER INFORMATION: 2' deoxy
<220> FEATURE:
<221> NAME/KEY: misc_feature
<222> LOCATION: (2)..(2)
<223> OTHER INFORMATION: 2' fluoro
```

```
<220> FEATURE:
<221> NAME/KEY: misc_feature
<222> LOCATION: (3)..(6)
<223> OTHER INFORMATION: 2' deoxy
<220> FEATURE:
<221> NAME/KEY: misc_feature
<222> LOCATION: (7)..(8)
<223> OTHER INFORMATION: 2' fluoro
<220> FEATURE:
<221> NAME/KEY: misc_feature
<222> LOCATION: (9)..(9)
<223> OTHER INFORMATION: 2' deoxy
<220> FEATURE:
<221> NAME/KEY: misc_feature
<222> LOCATION: (10)..(10)
<223> OTHER INFORMATION: 2' fluoro
<220> FEATURE:
<221> NAME/KEY: misc_feature
<222> LOCATION: (11)..(17)
<223> OTHER INFORMATION: 2' deoxy
<220> FEATURE:
<221> NAME/KEY: misc_feature
<222> LOCATION: (18)..(18)
<223> OTHER INFORMATION: 2' fluoro
<220> FEATURE:
<221> NAME/KEY: misc_feature
<222> LOCATION: (19)..(21)
<223> OTHER INFORMATION: 2' deoxy
<220> FEATURE:
<221> NAME/KEY: misc_feature
<222> LOCATION: (21)..(21)
<223> OTHER INFORMATION: inverted deoxy abasic

<400> SEQUENCE: 1
auaaggcuau gaagagauat t                                              21

<210> SEQ ID NO 2
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: ribose
<220> FEATURE:
<221> NAME/KEY: misc_feature
<222> LOCATION: (4)..(9)
<223> OTHER INFORMATION: 2' fluoro
<220> FEATURE:
<221> NAME/KEY: misc_feature
<222> LOCATION: (10)..(10)
<223> OTHER INFORMATION: 2' O-methyl
<220> FEATURE:
<221> NAME/KEY: misc_feature
<222> LOCATION: (11)..(11)
<223> OTHER INFORMATION: 2' fluoro
<220> FEATURE:
<221> NAME/KEY: misc_feature
<222> LOCATION: (12)..(13)
<223> OTHER INFORMATION: 2' O-methyl
<220> FEATURE:
<221> NAME/KEY: misc_feature
<222> LOCATION: (14)..(17)
<223> OTHER INFORMATION: 2' fluoro
<220> FEATURE:
<221> NAME/KEY: misc_feature
<222> LOCATION: (18)..(18)
<223> OTHER INFORMATION: 2' O-methyl
<220> FEATURE:
<221> NAME/KEY: misc_feature
<222> LOCATION: (19)..(19)
<223> OTHER INFORMATION: 2' fluoro
```

```
<220> FEATURE:
<221> NAME/KEY: misc_feature
<222> LOCATION: (20)..(21)
<223> OTHER INFORMATION: 2' O-methyl

<400> SEQUENCE: 2
uaucucuuca uagccuuauu u                                                    21

<210> SEQ ID NO 3
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted deoxy abasic
<220> FEATURE:
<221> NAME/KEY: misc_feature
<222> LOCATION: (1)..(4)
<223> OTHER INFORMATION: 2' O-methyl
<220> FEATURE:
<221> NAME/KEY: misc_feature
<222> LOCATION: (5)..(6)
<223> OTHER INFORMATION: 2' fluoro
<220> FEATURE:
<221> NAME/KEY: misc_feature
<222> LOCATION: (7)..(7)
<223> OTHER INFORMATION: 2' O-methyl
<220> FEATURE:
<221> NAME/KEY: misc_feature
<222> LOCATION: (8)..(9)
<223> OTHER INFORMATION: 2' fluoro
<220> FEATURE:
<221> NAME/KEY: misc_feature
<222> LOCATION: (10)..(14)
<223> OTHER INFORMATION: 2' O-methyl
<220> FEATURE:
<221> NAME/KEY: misc_feature
<222> LOCATION: (15)..(18)
<223> OTHER INFORMATION: 2' fluoro
<220> FEATURE:
<221> NAME/KEY: misc_feature
<222> LOCATION: (19)..(19)
<223> OTHER INFORMATION: 2' O-methyl
<220> FEATURE:
<221> NAME/KEY: misc_feature
<222> LOCATION: (20)..(21)
<223> OTHER INFORMATION: 2' deoxy
<220> FEATURE:
<221> NAME/KEY: misc_feature
<222> LOCATION: (20)..(21)
<223> OTHER INFORMATION: phophorothioate linkage
<220> FEATURE:
<221> NAME/KEY: misc_feature
<222> LOCATION: (21)..(21)
<223> OTHER INFORMATION: inverted deoxy abasic

<400> SEQUENCE: 3
cuuuaacaau uccugaaaut t                                                    21

<210> SEQ ID NO 4
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: ribose
```

```
<220> FEATURE:
<221> NAME/KEY: misc_feature
<222> LOCATION: (1)..(4)
<223> OTHER INFORMATION: phophorothioate linkage
<220> FEATURE:
<221> NAME/KEY: misc_feature
<222> LOCATION: (4)..(5)
<223> OTHER INFORMATION: 2' O-methyl
<220> FEATURE:
<221> NAME/KEY: misc_feature
<222> LOCATION: (6)..(10)
<223> OTHER INFORMATION: 2' fluoro
<220> FEATURE:
<221> NAME/KEY: misc_feature
<222> LOCATION: (11)..(12)
<223> OTHER INFORMATION: 2' O-methyl
<220> FEATURE:
<221> NAME/KEY: misc_feature
<222> LOCATION: (13)..(14)
<223> OTHER INFORMATION: 2' fluoro
<220> FEATURE:
<221> NAME/KEY: misc_feature
<222> LOCATION: (15)..(15)
<223> OTHER INFORMATION: 2' O-methyl
<220> FEATURE:
<221> NAME/KEY: misc_feature
<222> LOCATION: (16)..(19)
<223> OTHER INFORMATION: 2' fluoro
<220> FEATURE:
<221> NAME/KEY: misc_feature
<222> LOCATION: (20)..(21)
<223> OTHER INFORMATION: phophorothioate linkage
<220> FEATURE:
<221> NAME/KEY: misc_feature
<222> LOCATION: (20)..(21)
<223> OTHER INFORMATION: 2' O-methyl

<400> SEQUENCE: 4
auuucaggaa uuguuaaagu u                                                     21
```

LOW MOLECULAR WEIGHT CATIONIC LIPIDS FOR OLIGONUCLEOTIDE DELIVERY

BACKGROUND OF THE INVENTION

The present invention relates to novel cationic lipids that can be used in combination with other lipid components such as cholesterol and PEG-lipids to form lipid nanoparticles with oligonucleotides, to facilitate the cellular uptake and endosomal escape, and to knockdown target mRNA both in vitro and in vivo.

Cationic lipids and the use of cationic lipids in lipid nanoparticles for the delivery of oligonucleotides, in particular siRNA and miRNA, have been previously disclosed. Lipid nanoparticles and use of lipid nanoparticles for the delivery of oligonucleotides, in particular siRNA and miRNA, has been previously disclosed. Oligonucleotides (including siRNA and miRNA) and the synthesis of oligonucleotides has been previously disclosed. (See US patent applications: US 2006/0083780, US 2006/0240554, US 2008/0020058, US 2009/0263407 and US 2009/0285881 and PCT patent applications: WO 2009/086558, WO2009/127060, WO2009/132131, WO2010/042877, WO2010/054384, WO2010/054401, WO2010/054405 and WO2010/054406). See also Semple S. C. et al., Rational design of cationic lipids for siRNA delivery, Nature Biotechnology, published online 17 Jan. 2010; doi:10.1038/nbt.1602.

Other cationic lipids are disclosed in US patent applications: US 2009/0263407, US 2009/0285881, US 2010/0055168, US 2010/0055169, US 2010/0063135, US 2010/0076055, US 2010/0099738 and US 2010/0104629.

Traditional cationic lipids such as CLinDMA and DLinDMA have been employed for siRNA delivery to liver but suffer from non-optimal delivery efficiency along with liver toxicity at higher doses. It is an object of the instant invention to provide a cationic lipid scaffold that demonstrates enhanced efficacy along with lower liver toxicity as a result of lower lipid levels in the liver. The present invention employs low molecular weight cationic lipids with one short lipid chain to enhance the efficiency and tolerability of in vivo delivery of siRNA.

SUMMARY OF THE INVENTION

The instant invention provides for novel cationic lipids that can be used in combination with other lipid components such as cholesterol and PEG-lipids to form lipid nanoparticles with oligonucleotides. It is an object of the instant invention to provide a cationic lipid scaffold that demonstrates enhanced efficacy along with lower liver toxicity as a result of lower lipid levels in the liver. The present invention employs low molecular weight cationic lipids with one short lipid chain to enhance the efficiency and tolerability of in vivo delivery of siRNA.

DETAILED DESCRIPTION OF THE INVENTION

Figure 1:
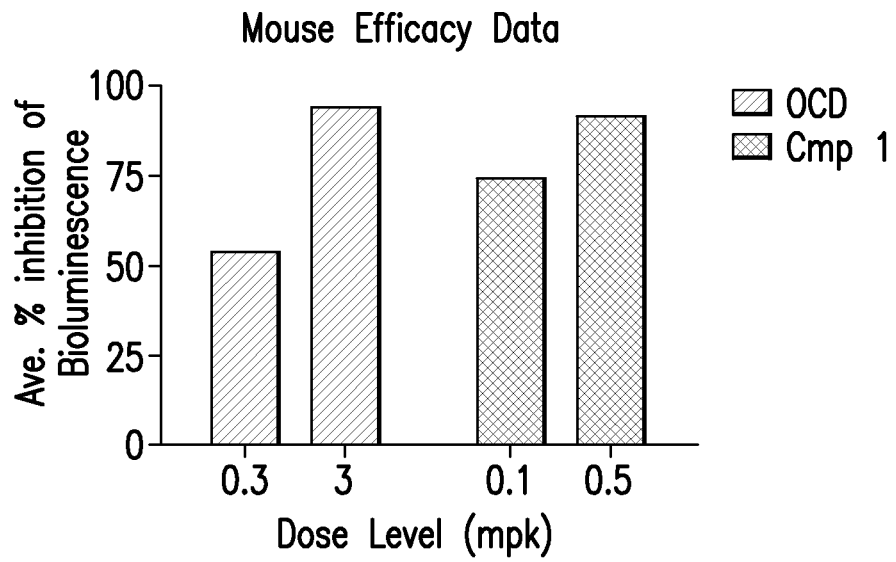
FIG. 1: LNP (Compound 1) efficacy in mice.

The various aspects and embodiments of the invention are directed to the utility of novel cationic lipids useful in lipid nanoparticles to deliver oligonucleotides, in particular, siRNA and miRNA, to any target gene. (See US patent applications: US 2006/0083780, US 2006/0240554, US 2008/0020058, US 2009/0263407 and US 2009/0285881 and PCT patent applications: WO 2009/086558, WO2009/127060, WO2009/132131, WO2010/042877, WO2010/054384, WO2010/054401, WO2010/054405 and WO2010/054406). See also Semple S. C. et al., Rational design of cationic lipids for siRNA delivery, Nature Biotechnology, published online 17 Jan. 2010; doi:10.1038/nbt.1602.

The cationic lipids of the instant invention are useful components in a lipid nanoparticle for the delivery of oligonucleotides, specifically siRNA and miRNA.

In a first embodiment of this invention, the cationic lipids are illustrated by the Formula A:

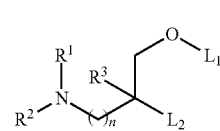

A wherein:
$R^1$ and $R^2$ are independently selected from H, $(C_1-C_6)$ alkyl, heterocyclyl, and polyamine, wherein said alkyl, heterocyclyl and polyamine are optionally substituted with one to three substituents selected from R', or $R^1$ and $R^2$ can be taken together with the nitrogen to which they are attached to form a monocyclic heterocycle with 4-7 members optionally containing, in addition to the nitrogen, one or two additional heteroatoms selected from N, O and S, said monocyclic heterocycle is optionally substituted with one to three substituents selected from R';

$R^3$ is selected from H and $(C_1-C_6)$alkyl, said alkyl optionally substituted with one to three substituents selected from R';

R' is independently selected from halogen, R", OR", SR", CN, $CO_2R$" and $CON(R")_2$;

R" is independently selected from H and $(C_1-C_6)$alkyl, wherein said alkyl is optionally substituted with halogen and OH;

n is 0, 1, 2, 3, 4 or 5; and $L_1$ and $L_2$ are independently selected from $C_3-C_{24}$ alkyl and $C_3-C_{24}$ alkenyl, said alkyl and alkenyl are optionally substituted with one or more substituents selected from Rt;

or any pharmaceutically acceptable salt or stereoisomer thereof.

In a second embodiment, the invention features a compound having Formula A, wherein:
$R^1$ and $R^2$ are each methyl;
$R^3$ is H;
n is 0;
$L_1$ is selected from $C_3-C_{24}$ alkyl and $C_3-C_{24}$ alkenyl; and
$L_2$ is selected from $C_3-C_9$ alkyl and $C_3-C_9$ alkenyl;
or any pharmaceutically acceptable salt or stereoisomer thereof.

In a third embodiment, the invention features a compound having Formula A,
wherein:
$R^1$ and $R^2$ are each methyl;
$R^3$ is H;
n is 0;
$L_1$ is selected from $C_3-C_9$ alkyl and $C_3-C_9$ alkenyl; and
$L_2$ is selected from $C_3-C_{24}$ alkyl and $C_3-C_{24}$ alkenyl;
or any pharmaceutically acceptable salt or stereoisomer thereof.

In a fourth embodiment, the invention features a compound having Formula A,
wherein:
$R^1$ and $R^2$ are each methyl;
$R^3$ is H;
n is 1;
$L_1$ is selected from $C_3$-$C_{24}$ alkyl and $C_3$-$C_{24}$ alkenyl; and
$L_2$ is selected from $C_3$-$C_9$ alkyl and $C_3$-$C_9$ alkenyl;
or any pharmaceutically acceptable salt or stereoisomer thereof.

In a fifth embodiment, the invention features a compound having Formula A,
wherein:
$R^1$ and $R^2$ are each methyl;
$R^3$ is H;
n is 2;
$L_1$ is selected from $C_3$-$C_{24}$ alkyl and $C_3$-$C_{24}$ alkenyl; and
$L_2$ is selected from $C_3$-$C_9$ alkyl and $C_3$-$C_9$ alkenyl;
or any pharmaceutically acceptable salt or stereoisomer thereof.

Specific cationic lipids are:
(2S)—N,N-dimethyl-1-[(9Z,12Z)-octadeca-9,12-dien-1-yloxy]undecan-2-amine (Compound 1);
(2S)-1-[(9Z,12Z)-octadeca-9,12-dien-1-yloxy]undecan-2-amine (Compound 2);
(2S)-1-[(9Z,12Z)-octadeca-9,12-dien-1-yloxy]dodecan-2-amine (Compound 3);
(2R)-1-[(9Z,12Z)-octadeca-9,12-lien-1-yloxy]dodecan-2-amine (Compound 4);
(2S)-1-[(9Z,12Z)-octadeca-9,12-dien-1-yloxy]decan-2-amine (Compound 5);
(2S)-1-[(9Z,12Z)-octadeea-9,12-dien-1-yloxy]nonan-2-amine (Compound 6);
(2S)—N,N-dimethyl-1-[(9Z,12Z)-octadeca-9,12-dien-1-yloxy]tridecan-2-amine (Compound 7);
(2S)—N,N-dimethyl-1-[(9Z,12Z)-octadeca-9,12-dien-1-yloxy]nonan-2-amine (Compound 8);
(2R)—N,N-dimethyl-1-[(9Z,12Z)-octadeca-9,12-dien-1-yloxy]dodecan-2-amine (Compound 9);
(2S)—N,N-dimethyl-1-[(9Z,12Z)-octadeca-9,12-dien-1-yloxy]dodecan-2-amine (Compound 10);
(2S)—N,N-dimethyl-1-[(9Z,12Z)-octadeca-9,12-dien-1-yloxy]decan-2-amine (Compound 11); and
(2S,12Z,15Z)—N,N-dimethyl-1-(octyloxy)henicosa-12,15-dien-2-amine (Compound 12);
(2R,12Z,15Z)-1-(decyloxy)-N,N-dimethylhenicosa-12,15-dien-2-amine (Compound 13);
(2R,12Z,15Z)-1-(hexyloxy)-N,N-dimethylhenicosa-12,15-dien-2-amine (Compound 14);
(2R,12Z,15Z)-1-(hexadecyloxy)-N,N-dimethylhenicosa-12,15-dien-2-amine (Compound 15);
(2R,12Z,15Z)—N,N-dimethyl-1-(undecyloxy)henicosa-12,15-dien-2-amine (Compound 16);
N,N-dimethyl-2-{[(9Z,12Z)-octadeca-9,12-dien-1-yloxy]methyl}undecan-1-amine (Compound 17);
N,N-dimethyl-3-{[(9Z,12Z)-octadeca-9,12-dien-1-yloxy]methyl}dodecan-1-amine (Compound 18); and
(2S)—N,N-dimethyl-1-({8-[(1R,2R)-2-{[(1S,2S)-2-pentylcyclopropyl]methyl}cyclopropyl]octyl}oxy)tridecan-2-amine (Compound 19);
or any pharmaceutically acceptable salt or stereoisomer thereof.

In another embodiment, the cationic lipids disclosed are useful in the preparation of lipid nanoparticles.

In another embodiment, the cationic lipids disclosed are useful components in a lipid nanoparticle for the delivery of oligonucleotides.

In another embodiment, the cationic lipids disclosed are useful components in a lipid nanoparticle for the delivery of siRNA and miRNA.

In another embodiment, the cationic lipids disclosed are useful components in a lipid nanoparticle for the delivery of siRNA.

The cationic lipids of the present invention may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention. In addition, the cationic lipids disclosed herein may exist as tautomers and both tautomeric forms are intended to be encompassed by the scope of the invention, even though only one tautomeric structure is depicted.

It is understood that substituents and substitution patterns on the cationic lipids of the instant invention can be selected by one of ordinary skill in the art to provide cationic lipids that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

It is understood that one or more Si atoms can be incorporated into the cationic lipids of the instant invention by one of ordinary skill in the art to provide cationic lipids that are chemically stable and that can be readily synthesized by techniques known in the art from readily available starting materials.

In the compounds of Formula A, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula A. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula A can be prepared without undue experimentation by conventional techniques well known to those skilled in the art or by processes analogous to those described in the Scheme and Examples herein using appropriate isotopically-enriched reagents and/or intermediates.

As used herein, "alkyl" means a straight chain, cyclic or branched saturated aliphatic hydrocarbon having the specified number of carbon atoms.

As used herein, "alkenyl" means a straight chain, cyclic or branched unsaturated aliphatic hydrocarbon having the specified number of carbon atoms including but not limited to diene, triene and tetraene unsaturated aliphatic hydrocarbons.

Examples of a cyclic "alkyl" or "alkenyl are:

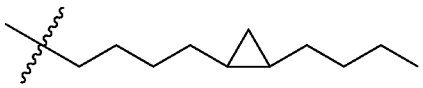

-continued

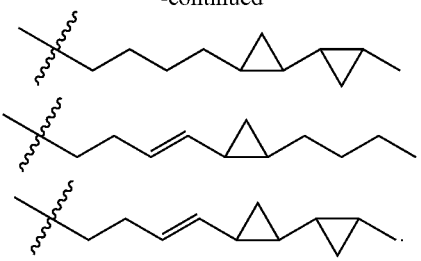

As used herein, "heterocyclyl" or "heterocycle" means a 4- to 10-membered aromatic or nonaromatic heterocycle containing from 1 to 4 heteroatoms selected from the group consisting of O, N and S, and includes bicyclic groups. "Heterocyclyl" therefore includes, the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof all of which are optionally substituted with one to three substituents selected from R".

As used herein, "polyamine" means compounds having two or more amino groups. Examples include putrescine, cadaverine, spermidine, and spermine.

As used herein, "halogen" means Br, Cl, F and I.

In an embodiment of Formula A, $R^1$ and $R^2$ are independently selected from H and $(C_1-C_6)$alkyl, wherein said alkyl is optionally substituted with one to three substituents selected from or $R^1$ and $R^2$ can be taken together with the nitrogen to which they are attached to form a monocyclic heterocycle with 4-7 members optionally containing, in addition to the nitrogen, one or two additional heteroatoms selected from N, O and S, said monocyclic heterocycle is optionally substituted with one to three substituents selected from R'.

In an embodiment of Formula A, $R^1$ and $R^2$ are independently selected from H, methyl, ethyl and propyl, wherein said methyl, ethyl and propyl are optionally substituted with one to three substituents selected from R', or $R^1$ and $R^2$ can be taken together with the nitrogen to which they are attached to form a monocyclic heterocycle with 4-7 members optionally containing, in addition to the nitrogen, one or two additional heteroatoms selected from N, and S, said monocyclic heterocycle is optionally substituted with one to three substituents selected from $R^1$.

In an embodiment of Formula A, $R^1$ and $R^2$ are independently selected from H, methyl, ethyl and propyl.

In an embodiment of Formula A, $R^1$ and $R^2$ are each methyl.

In an embodiment of Formula A, $R^3$ is selected from H and methyl.

In an embodiment of Formula A, $R^3$ is H.

In an embodiment of Formula A, R' is R".

In an embodiment of Formula A, R" is independently selected from H, methyl, ethyl and propyl, wherein said methyl, ethyl and propyl are optionally substituted with one or more halogen and OH.

In an embodiment of Formula A, R" is independently selected from H, methyl, ethyl and propyl.

In an embodiment of Formula A, n is 0, 1 or 2.

In an embodiment of Formula A, n is 0 or 1.

In an embodiment of Formula A, n is 0.

In an embodiment of Formula A, $L_1$ is selected from $C_3-C_{24}$ alkyl and $C_3-C_{24}$ alkenyl, which are optionally substituted with halogen and OH.

In an embodiment of Formula A, $L_1$ is selected from $C_3-C_{24}$ alkyl and $C_3-C_{24}$ alkenyl.

In an embodiment of Formula A, $L_1$ is selected from $C_3-C_{24}$ alkenyl.

In an embodiment of Formula A, $L_1$ is selected from $C_{12}-C_{24}$ alkenyl.

In an embodiment of Formula A, $L_1$ is $C_{18}$ alkenyl.

In an embodiment of Formula A, $L_1$ is:

In an embodiment of Formula A, $L_1$ is $C_8$ alkyl.

In an embodiment of Formula A, $L_2$ is selected from $C_3-C_{24}$ alkyl and $C_3-C_{24}$ alkenyl, which are optionally substituted with halogen and OH.

In an embodiment of Formula A, $L_2$ is selected from $C_3-C_{24}$ alkyl and $C_3-C_{24}$ alkenyl.

In an embodiment of Formula A, $L_2$ is selected from $C_3-C_{24}$ alkenyl.

In an embodiment of Formula A, $L_2$ is selected from $C_{12}-C_{24}$ alkenyl.

In an embodiment of Formula A, $L_2$ is $C_{19}$ alkenyl.

In an embodiment of Formula A, $L_2$ is:

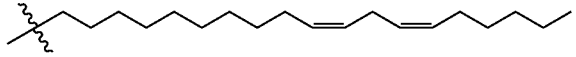

In an embodiment of Formula A, $L_2$ is selected from $C_3-C_9$ alkyl and $C_3-C_9$ alkenyl, which are optionally substituted with halogen and OH.

In an embodiment of Formula A, $L_2$ is selected from $C_5-C_9$ alkyl and $C_5-C_9$ alkenyl, which are optionally substituted with halogen and OH.

In an embodiment of Formula A, $L_2$ is selected from $C_7-C_9$ alkyl and $C_7-C_9$ alkenyl, which are optionally substituted with halogen and OH.

In an embodiment of Formula A, $L_2$ is selected from $C_3-C_9$ alkyl and $C_3-C_9$ alkenyl.

In an embodiment of Formula A, $L_2$ is selected from $C_5-C_9$ alkyl and $C_5-C_9$ alkenyl.

In an embodiment of Formula A, $L_2$ is selected from $C_7-C_9$ alkyl and $C_7-C_9$ alkenyl.

In an embodiment of Formula A, $L_2$ is $C_3-C_9$ alkyl.

In an embodiment of Formula A, $L_2$ is $C_5-C_9$ alkyl.

In an embodiment of Formula A, $L_2$ is $C_7$-$C_9$ alkyl.

In an embodiment of Formula A, $L_2$ is $C_9$ alkyl.

In an embodiment of Formula A, "heterocyclyl" is pyrrolidine, piperidine, morpholine, imidazole or piperazine.

In an embodiment of Formula A, "monocyclic heterocyclyl" is pyrrolidine, piperidine, morpholine, imidazole or piperazine.

In an embodiment of Formula A, "polyamine" is putrescine, cadaverine, spermidine or spermine.

In an embodiment, "alkyl" is a straight chain saturated aliphatic hydrocarbon having the specified number of carbon atoms.

In an embodiment, "alkenyl" is a straight chain unsaturated aliphatic hydrocarbon having the specified number of carbon atoms.

Included in the instant invention is the free form of cationic lipids of Formula A, as well as the pharmaceutically acceptable salts and stereoisomers thereof. Some of the isolated specific cationic lipids exemplified herein are the protonated salts of amine cationic lipids. The term "free form" refers to the amine cationic lipids in non-salt form. The encompassed pharmaceutically acceptable salts not only include the isolated salts exemplified herein for the specific cationic lipids described herein, but also all the typical pharmaceutically acceptable salts of the free form of cationic lipids of Formula A. The free form of the specific salt cationic lipids described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant cationic lipids can be synthesized from the cationic lipids of this invention which contain a basic or acidic moiety by conventional chemical methods. Generally, the salts of the basic cationic lipids are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the cationic lipids of this invention include the conventional non-toxic salts of the cationic lipids of this invention as formed by reacting a basic instant cationic lipids with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic (TFA) and the like.

When the cationic lipids of the present invention are acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the cationic lipids of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

EXAMPLES

Examples provided are intended to assist in a further understanding of the invention. Particular materials employed, species and conditions are intended to be further illustrative of the invention and not limitative of the reasonable scope thereof. The reagents utilized in synthesizing the cationic lipids are either commercially available or are readily prepared by one of ordinary skill in the art.

Synthesis of the novel cationic lipids is a linear process starting from epichlorohydrin (i) (General Scheme 1). Epoxide opening, ring closure with lipid alkoxide delivers epoxy ether intermediate ii. Grignard addition to the epoxide provides secondary alcohol intermediate iii. Mitsinobu inversion with azide followed by reduction yields primary amine intermediates v. Reductive amination provides the tertiary amine derivatives vi.

GENERAL SCHEME 1

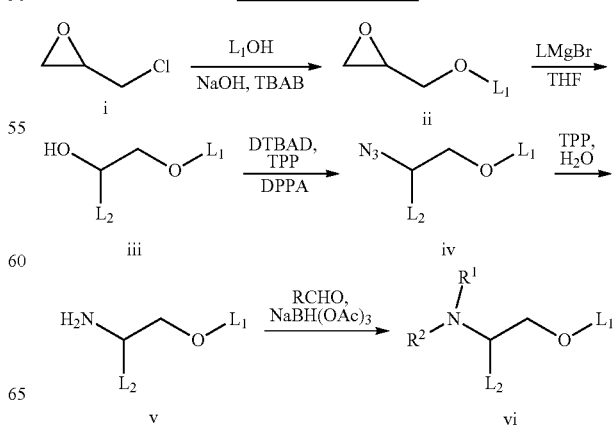

An alternative synthesis of the novel cationic lipids starting from epichlorohydrin (i) is depicted in General Scheme 2. Epoxide opening, ring closure with lipid Grignard delivers epoxide intermediate vii. Alkoxide addition to the epoxide provides secondary alcohol intermediate iii. Mitsinobu inversion with azide followed by reduction yields primary amine intermediates v. Reductive amination provides the tertiary amine derivatives vi.

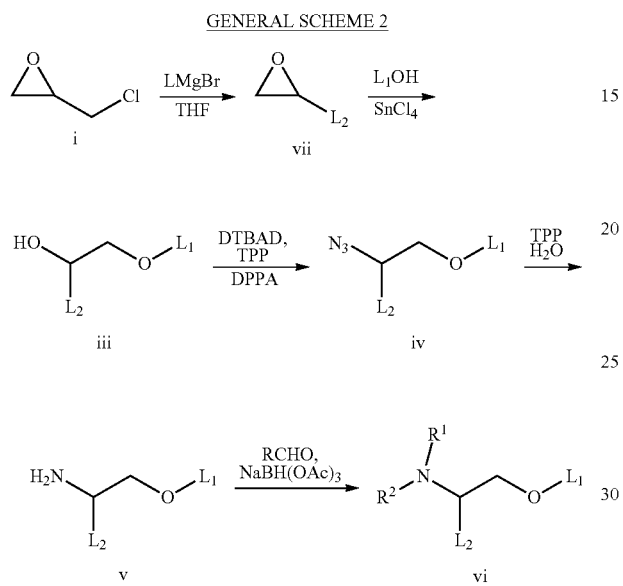

Synthesis of the homologated cationic lipids x (General Scheme 3) begins with oxidation of intermediate iii to ketone vii using Dess-Martin Periodinane. Conversion of the ketone to the nitrile viii is accomplished with TOSMIC. Reduction of the nitrile with lithium aluminum hydride gives primary amine ix. Reductive amination provides cationic lipids x.

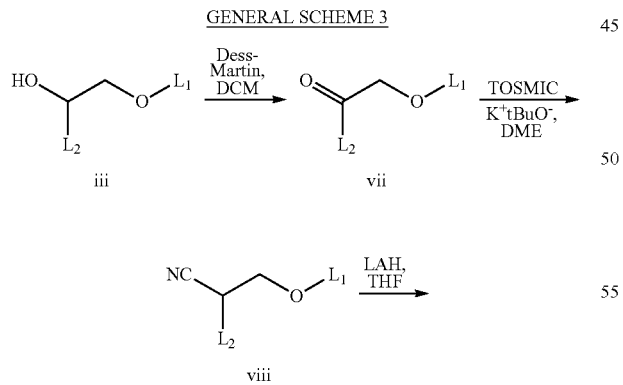

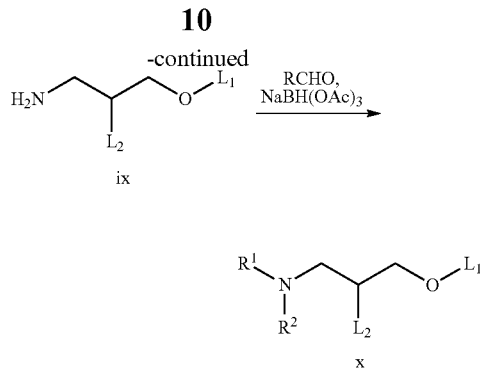

Synthesis of doubly homologated cationic lipids xiii begins with ketone vii. Peterson olefination generates the unsaturated amide xi. Conjugate reduction with L-Selectride gives amide xii. Amide reduction with lithium aluminum hydride gives cationic lipids xiii.

GENERAL SCHEME 4

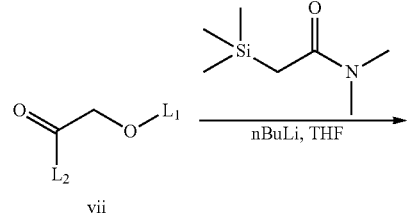

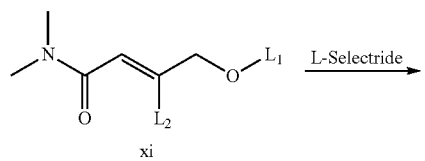

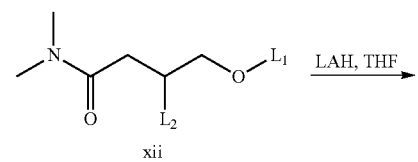

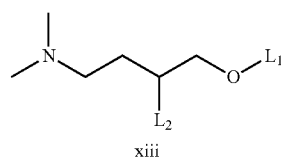

2S)—N,N-dimethyl-1-[(9Z,12Z)-oetadeca-9,12-dien-1-yloxy]undecan-2-amine (Compound 1)

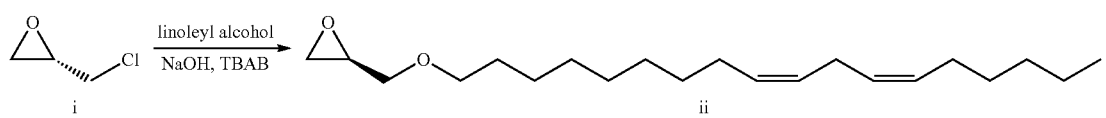 [SMILES: ClC[C@@H]1CO1 ; CCCCC/C=C\C/C=C\CCCCCCCCOC[C@H]1CO1]

A 250 mL rb flask was charged with magnetic stirbar, tetrabutyl ammonium bromide (TBAB, 2.72 g, 8.4 mmol), linoleyl alcohol (225 g, 884 mmol), and sodium hydroxide (50.7 g, 1.2 mol), then cooled in an ice bath. The (S)-epichlorohydrin (156 g, 1.69 mol) was added slowly over 2 hours and then warmed to ambient temperature and stirred overnight. 259 mL of hexane was added and allowed to stir for 15 mins, then mixture was filtered and organic layer was concentrated in vacuo. The product was purified using 0-10% ethyl acetate/hexane gradient on 330 g silica column to give (2R)-2-{[(9Z, 12Z)-octadeca-9,12-dien-1-yloxy]methyl}oxirane. $^1$H NMR (CDCl$_3$, 300 mHz) δ 0.90-0.86 (m, 3H), 1.29 (s, 16H), 1.55-1.64 (m, 2H), 2.00-2.07 (m, 4H), 2.58-2.61 (m, 1H), 2.74-2.80 (m, 3H), 3.12-3.15 (m, 1H) 3.34-3.52 (m, 3H), 3.67-3.72 (dd, J=12 Hz, 1H) 5.30-5.35 (m, 4H); HRMS (m+1) calcd 323.2872. Found 323.2951.

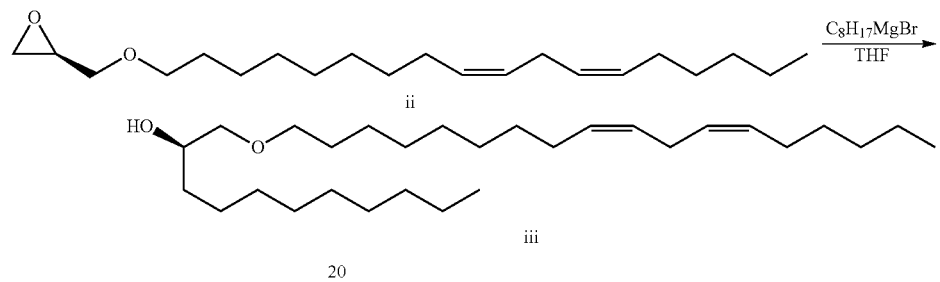

The epoxide (15 g, 46.5 mmol) was dissolved in THF and cooled to 0° C. under stream of Nitrogen. Octyl Grignard (25.6 mL 2M solution, 51.2 mmol) was added dropwise and then heate in microwave at 120° C. for one hour. The precipitate was filtered off and the solvent evaporated in vacuo. The crude oil was directly loaded onto a silica gel column and eluted with 0-10% gradient (hexane-ethyl acetate) to give (2R)-1-[(9Z,12Z)-octadeca-9,12-dien-1-yloxy]undecan-2-ol. LC/MS (m+1)=437.6.

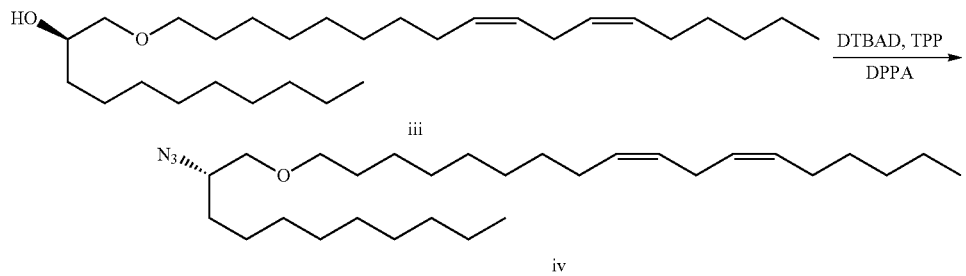

Triphenyl phosphine (14.4 g, 55 mmol) was dissolved in THF and cooled to 0° C. under nitrogen. Di-tertbutyl azodicarboxylate (13.7 g, 59.5 mmol) was added slowly and the reaction was stirred for 30 mins. Then the alcohol (20 g, 45.8 mmol) was added dropwise and allowed to stir for 10 mins, then diphenyl phosphorylazide (15.1 g, 55 mmol) was added and allowed to stir overnight, warming to ambient temperature. The reaction was evaporated to dryness in vacuo and directly loaded onto a silica gel column and eluted with 0-10% ethyl acetate/hexane gradient to provide (2S)-2-azidoundecyl(9Z,12Z)-octadeca-9,12-dien-1-yl ether which was carried directly into the next reaction without characterization.

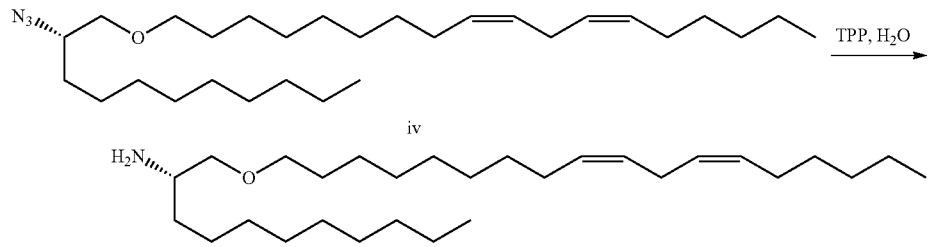

Triphenyl phosphine (4.54 g, 17.3 mmol) and the azide (8 g, 17.3 mmol) were dissolved in THF. The reaction mixture was split into 3 μw tubes and irradiated at 120° C. for 1 hour each. Considerable pressure built in each tube so care should be noted. LC indicated 100% conversion to phosphoimine intermediate. To each tube was added ~3 mL of water and the reaction irradiated for 10 min at 120° C. The reaction mixtures were combined and concentrated to remove organic solvent. Hexane was added to precipitate phosphine oxides which were filtered through cintered glass funnel. The solvent was then removed in vacuo. The crude product was purified using HPLC with 30 min run and 60-100% water/acetonitrile gradient. The combined HPLC fractions were neutralized with sodium bicarbonate evaoporated in vacuo. The pure product was partitioned between water/hexanes. The organic layer was dried over sodium sulfate, filtered and evaporated in vacuo to afford (2S)-1-[(9Z,12Z)-octadeca-9,12-dien-1-yloxy]undecan-2-amine (2). $^1$H NMR (CDCl$_3$, 300 mHz) δ 0.88-0.87 (m, 6H), 1.25-1.29 (s, 32H), 1.54-1.54 (m, 2H), 2.03-2.05 (m, 4H), 2.23 (s, 2H), 2.75-2.76 (m, 2H), 2.96 (m, 1H), 3.13-3.18 (m, 1H), 3.38-3.45 (m, 3H), 5.31-5.38 (m, 4H); LC/MS (m+1) 436.7.

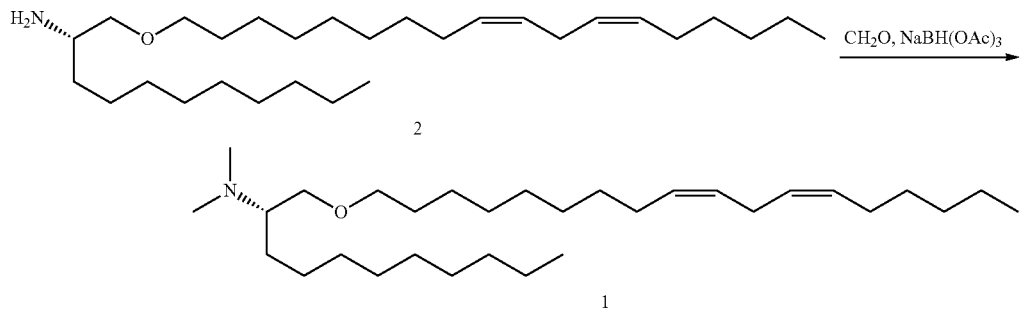

The primary amine (3.5 g, 8 mmol) was dissolved in THF and formaldehyde (3.26 g, 40.2 mmol) was added, followed by triacetoxy borohydride (5.1 g, 24.1 mmol). The reaction was stirred at ambient temperature for 15 mins. LC/MS indicated 100% conversion to product. Added 1M NaOH until basic and extracted with hexane and washed with water. Retained organic layer and removed solvent in vacuo. Purified using 60-100% water/acetonitrile 30 min gradient on C8 HPLC. Combined fractions and added sodium bicarbonate and evaporated organics in vacuo. The product was partitioned between water/hexanes and the organics were dried over sodium sulfate, filtered and evaporated in vacuo to deliver (2S)—N,N-dimethyl-1-[(9Z,12Z)-octadeca-9,12-dien-1-yloxy]undecan-2-amine (1). $^1$H NMR (CDCl$_3$, 300 mHz) δ 0.88-0.87 (m, 6H), 1.285 (s, 33H), 1.55 (m, 2H), 1.80 (m, 1H), 2.00-2.05 (s, 4H), 2.29-2.31 (2H), 2.50 (m, 1H), 2.76-1.77 (m, 2H), 3.36-3.51 (m, 6H), 5.34-5.36 (m, 4H); LC/MS (m+1) 464.9.

Compounds 3-11 are novel cationic lipids and were prepared according to General Scheme 1 above.

| Compound | Structure | LC/MS (m + 1) |
|---|---|---|
| 3 | 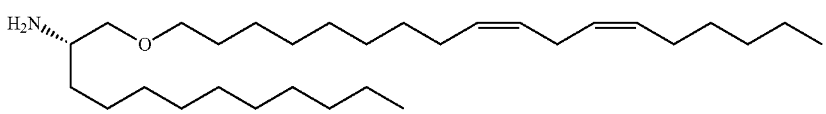 [SMILES: CCCCC/C=C\C/C=C\CCCCCCCCOC[C@@H](N)CCCCCCCCCC] | 450.4 |
| 4 | 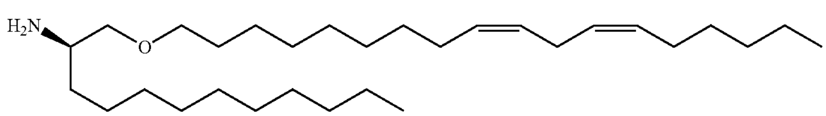 [SMILES: CCCCC/C=C\C/C=C\CCCCCCCCOC[C@H](N)CCCCCCCCCC] | 450.6 |
| 5 | 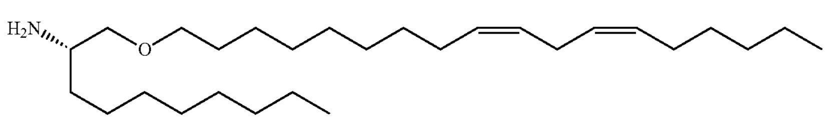 [SMILES: CCCCC/C=C\C/C=C\CCCCCCCCOC[C@@H](N)CCCCCCCC] | 423.6 |

| Compound | Structure | LC/MS (m + 1) |
|---|---|---|
| 6 | 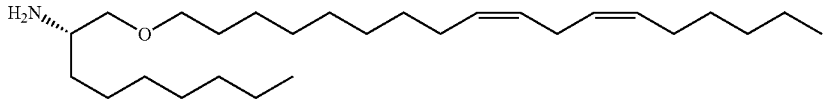 [SMILES: CCCCC/C=C\C/C=C\CCCCCCCCOC[C@@H](N)CCCCCCC] | 408.6 |
| 7 | 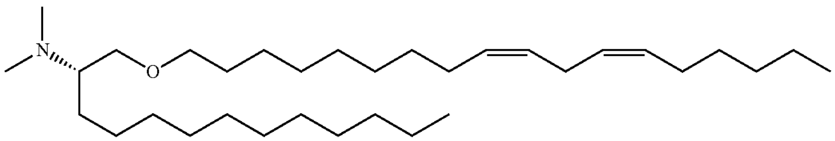 [SMILES: CCCCC/C=C\C/C=C\CCCCCCCCOC[C@H](CCCCCCCCCCC)N(C)C] | 492.8 |
| 8 | 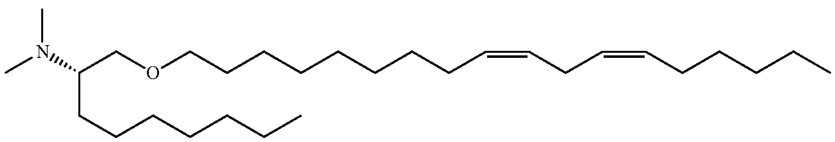 [SMILES: CCCCC/C=C\C/C=C\CCCCCCCCOC[C@H](CCCCCCC)N(C)C] | 436.6 |
| 9 | 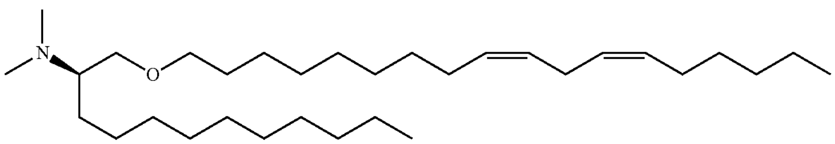 [SMILES: CCCCC/C=C\C/C=C\CCCCCCCCOC[C@@H](CCCCCCCCCC)N(C)C] | 479.7 |
| 10 | 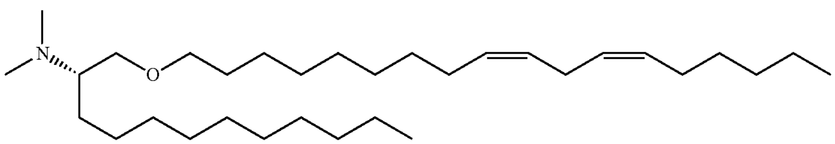 [SMILES: CCCCC/C=C\C/C=C\CCCCCCCCOC[C@H](CCCCCCCCCC)N(C)C] | 478.7 |
| 11 | 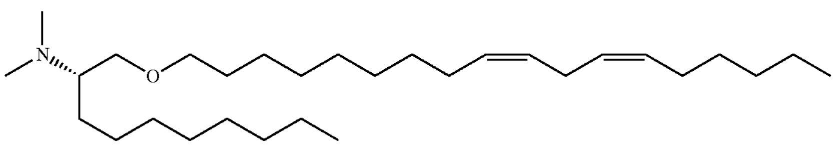 [SMILES: CCCCC/C=C\C/C=C\CCCCCCCCOC[C@H](CCCCCCCC)N(C)C] | 451.7 |

2S)—N,N-dimethyl-1-[(9Z,12Z)-octadeca-9,12-dien-1-yloxy]undecan-2-amine (Compound 12

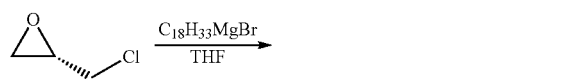

i

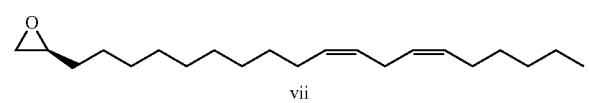

vii

A round bottomed flask was charged with magnetic stir bar, copper cyanide (1.45 g, 16.2 mmol), epichlorohydrin (15 g, 162 mmol) and purged with nitrogen. THF was added, the solution cooled to −78° C. and linoleyl Grignard (68.8 g, 195 mmol) was added slowly. After addition of Grignard the reaction was allowed to warm to ambient temperature. The reaction was quenched with saturated ammonium chloride solution and extracted with ether. The organics were dried over sodium sulfate, filtered and evaporated in vacuo. The intermediate chloro-alcohol was purified via flash chromatography (silica, 0-35% ethyl acetate/hexanes). The alcohol was dissolved in THF and allowed to stir with solid NaOH pellets at ambient temperature for 16 hours, then filtered off NaOH and washed organic layer with water. The organics were dried over sodium sulfate, filtered and evaporated in vacuo to provide (2S)-2-[(10Z,13Z)-nonadeca-10,13-dien-1-yl]oxirane. $^1$H NMR (CDCl$_3$, 300 mHz) δ 0.87-0.90 (m, 3H), 1.27-1.52 (m, 22H), 2.01-2.19 (m, 4H), 2.40-2.46 (m, 1H), 2.71-2.76 (m, 3H), 2.89-2.91 (m, 1H), 5.30-5.36 (m, 4H); LC/MS (m+H+acetonitrile) 349.5.

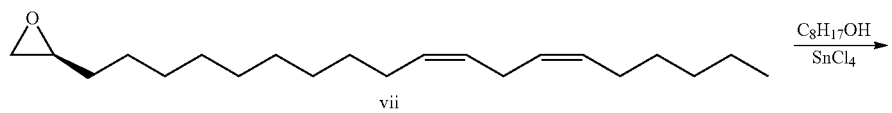

vii

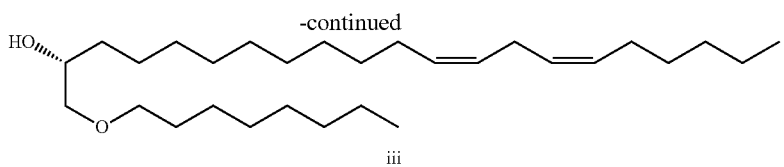

iii

The alcohol (2.55 g, 19.6 mmol) was dissolved in DCM and cooled to 0° C. To this solution was added tin chloride (1.63 mmol, 1.63 mL of a 1M solution). The epoxide (5 g, 16.3 mmol) was added to the reaction mixture dropwise and the reaction was aged for 1 hour at 0° C. The reaction was evaporated in vacuo, dissolved in hexanes and purified by flash chromatography (0-20% ethyl acetate/hexanes) to give (2R,12Z,15Z)-1-(octyloxy)henicosa-12,15-dien-2-ol. LC/MS (m+H)=437.6.

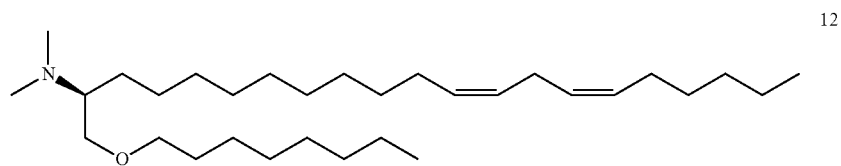 [SMILES: CCCCC/C=C\C/C=C\CCCCCCCCC[C@@H](COCCCCCCCC)N(C)C]

12

The alcohol was carried on to final Compound 12 as described for Compound 1. $^1$H NMR (CDCl$_3$, 300 mHz) δ 0.85-0.091 (m, 6H), 1.272 (s, 34H), 1.46 (m, 1H), 1.57 (m, 1H), 1.65 (s, 4H), 2.01-2.08 (3H), 2.30 (m, 6H), 2.52 (m, 1H), 2.75-2.79 (m, 2H), 3.29-3.4 (m, 2H), 3.46-3.51 (dd, 9.76 Hz, 1H), 5.30-5.39 (m, 4H); LC/MS (m+H)=464.7.

Compounds 13-16 are novel cationic lipids and were prepared according to General Scheme 2 above.

| Compound | Structure | LC/MS (m + 1) |
|---|---|---|
| 13 | 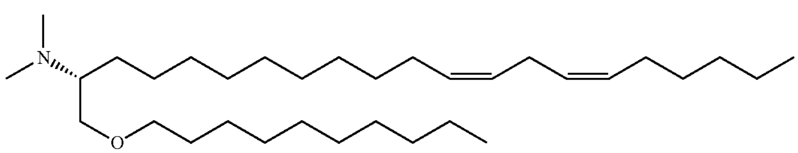 [SMILES: CCCCC/C=C\C/C=C\CCCCCCCCC[C@H](COCCCCCCCCCC)N(C)C] | 492.7 |
| 14 | 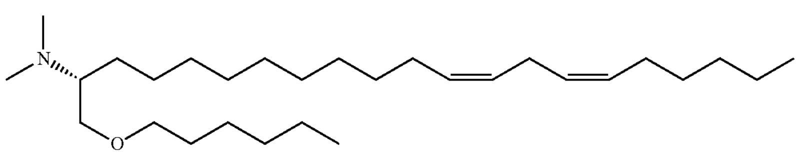 [SMILES: CCCCC/C=C\C/C=C\CCCCCCCCC[C@H](COCCCCCC)N(C)C] | 436.7 |
| 15 | 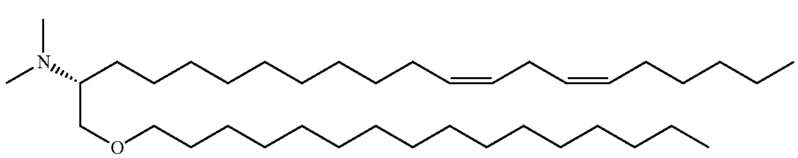 [SMILES: CCCCC/C=C\C/C=C\CCCCCCCCC[C@H](COCCCCCCCCCCCCCCCC)N(C)C] | 577.0 |
| 16 | 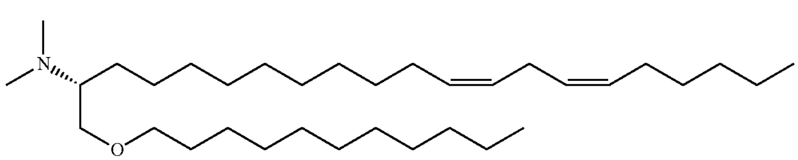 [SMILES: CCCCC/C=C\C/C=C\CCCCCCCCC[C@H](COCCCCCCCCCCC)N(C)C] | 506.8 |

N,N-dimethyl-2-{[(9Z,12Z)-octadeca-9,12-dien-1-yloxy]methyl}undecan-1-amine (Compound 17)

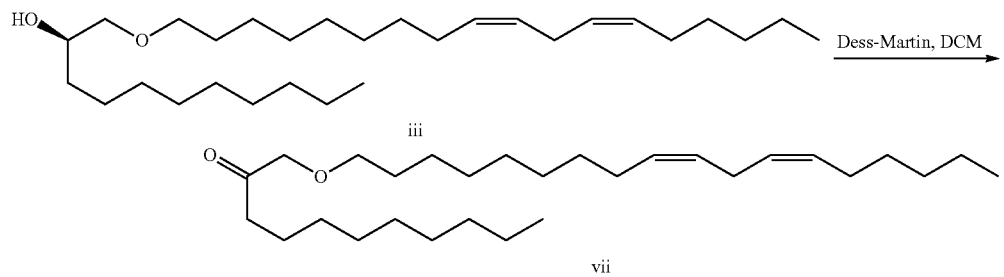

To a solution of alcohol iii (15 g, 34.3 mmol) in dichloromethane (50 mL) was added Doss-Martin Periodinane (14.6 g, 34.3 mmol) and the reaction was stirred at ambient temperature for 16 hours. The solids were filtered and the filtrate partitioned between water/DCM. The organics were dried over sodium sulfate, filtered and evaporated in vacuo. Purification by flash chromatography (silica, 0-15% ethyl acetate/hexanes) gave ketone vii. LC/MS (M+H)=435.6.

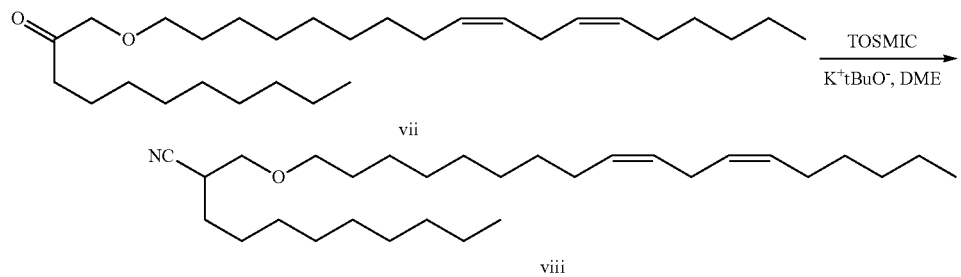

To a solution of ketone vii (10 g, 23.0 mmol) in DME (40 mL) was added TOSMIC (5.8 g, 29.9 mmol) and the solution was cooled to 0° C. To the cooled solution was added potassium tert-butoxide (46 mmol, 46 mL of a 1M solution in tBuOH) dropwise. After 30 minutes the reaction was partitioned between hexanes and water. The organics were dried over sodium sulfate, filtered and evaporated in vacuo. Purification by flash chromatography (silica, 0-10% ethyl acetate/hexanes) gave nitrile viii. LC/MS (M+H)=446.6.

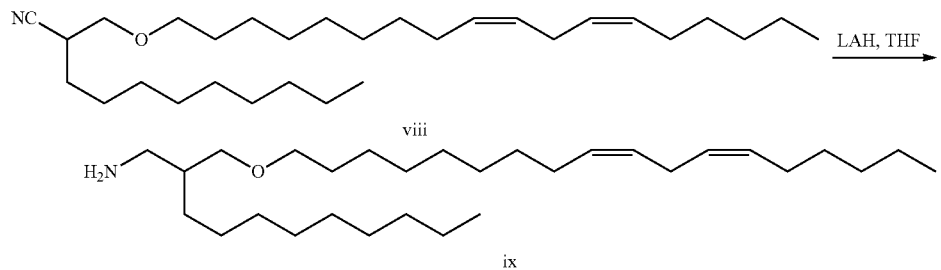

To a solution of nitrile viii (4.6 g, 10.4 mmol) in THF (25 mL) was added lithium aluminum hydride (0.8 g, 20.7 mmol) at ambient temperature. The reaction was quenched with sodium sulfate decahydrate solution and the solids were filtered. The filtrate was dried over sodium sulfate, filtered and evaporated in vacuo to give crude amine ix which was carried directly into next reaction. LC/MS (M+H)=450.6.

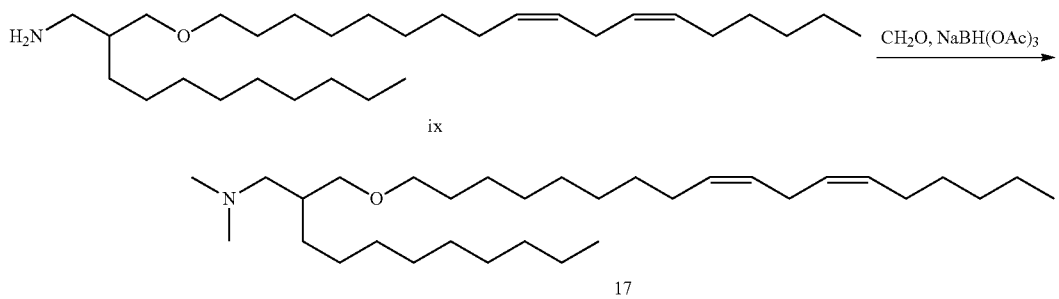

A solution of amine ix (4.7 g, 10.3 mmol) and formaldehyde (2.5 g, 31.1 mmol) in THF (25 mL) was treated with sodium triacetoxyborohydride (6.6 g, 31.1 mmol) at ambient temperature. After aging for 15 minutes, the reaction was quenched with 1M sodium hydroxide and partitioned between water and hexanes. The organics were dried over sodium sulfate, filtered and evaporated in vacuo. Purification by preparative reverse phase chromatography (C8 column, acetonitrile/water gradient) gave compound 17. LC/MS (M+H)=479.6. $^1$H NMR (CDCl$_3$, 400 mHz) δ 5.36 (m, 4H), 3.38 (m, 3H), 3.26 (m, 1H), 2.75 (t, J=6.4 Hz, 2H), 2.22 (m, 1H), 2.19 (s, 6H), 2.04 (m, 5H), 1.71 (m, 1H), 1.54 (m, 2H), 1.28 (m, 32H), 0.83 (m, 6H).

N,N-dimethyl-3-{[(9Z,12Z)-octadeca-9,12-dien-1-yloxy]methyl}dodecan-1-amine (Compound 18)

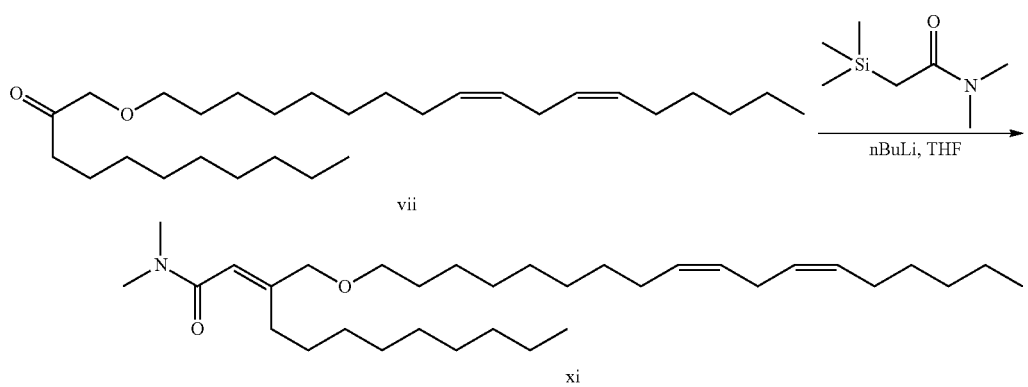

A solution of silyl amide (12.4 g, 78 mmol) in THF (50 mL) was cooled to −78° C. and treated with nBuLi (62.4 mmol, 25 mL of a 2.5M solution) and aged for 10 minutes. To this solution was transferred ketone vii (12 g, 27.6 mmol) in a small portion of dry THF. The reaction was aged 15 minutes then warmed to ambient temperature, quenched with sodium bicarbonate solution and partitioned between water and hexanes. The organics were dried over sodium sulfate, filtered and evaporated in vacuo to give amide xi. LC/MS (M+H)= 505.6.

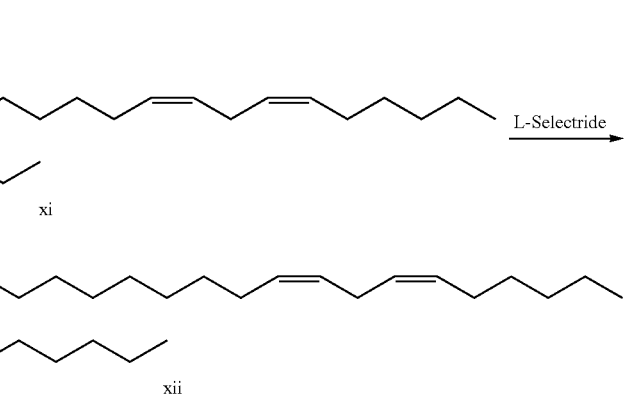

Amide xi (7 g, 13.9 mmol) was treated with L-Selectride (55.6 mmol, 55.6 mL of a 1M solution) in a microwave vial. The reaction was sealed and irradiated in a microwave reaction set at 70° C. for 16 hours. The reaction was then diluted with dichloromethane and quenched by careful addition of sodium perborate solid until effervescence stopped. The solids were filtered and the filtrate evaporated in vacuo to give xii. LC/MS (M+Fl)=507.6.

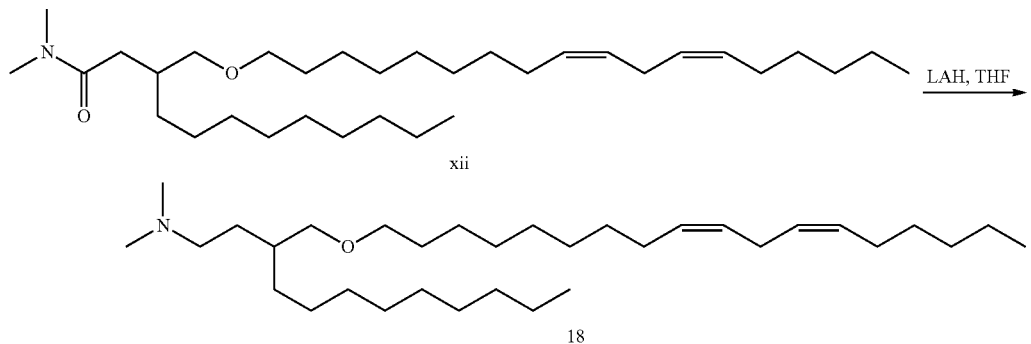

To a solution of amide xii (7 g, 13.8 mmol) in THF (30 mL) was added lithium aluminum hydride (1.1 g, 27.7 mmol). The reaction was quenched with sodium sulfate decahydrate solution and the solids filtered. The organics were evaporated in vacuo and the product purified by preparative reverse phase chromatography (C8 column, acetonitrile/water gradient) to give compound 18. LC/MS (M+H)=493.6. $^1$H NMR (CDCl$_3$, 400 mHz) δ 5.38 (m, 4H), 3.38 (m, 2H), 3.26 (m, 2H), 2.78 (t, J=6.4 Hz, 2H), 2.25 (m, 8H), 2.04 (m, 4H), 1.56 (m, 4H), 1.29 (m, 32H), 0.89 (m, 6H).

2S)—N,N-dimethyl-1-[(8-{2-[(2-pentylcyclopropyl)methyl]cyclopropyl}octyl)oxy]tridecan-2-amine (Compound 19

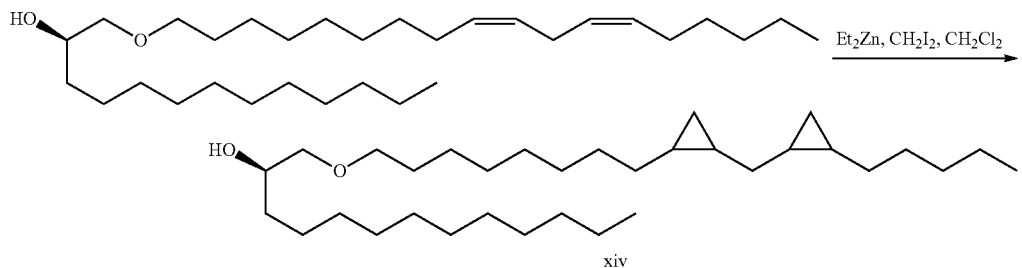

A solution of diene (24 g, 51.6 mmol) in dichloromethane (100 mL) was cooled to −15° C. To this solution was added diethyl zinc (310 mmol, 310 mL of a 1M solution) followed by diiodomethane (25 mL, 310 mmol) and the reaction was aged for 16 hours while slowly warming to ambient temperature. The reaction was quenched with ammonium chloride solution and partitioned between water and dichloromethane. The organics were dried over sodium sulfate, filtered and evaporated in vacuo. Purification by flash chromatography (silica, 0-25% ethyl acetate/hexanes) gave bis-cyclopropane intermediate xiv. LC/MS (M+H) 493.6.

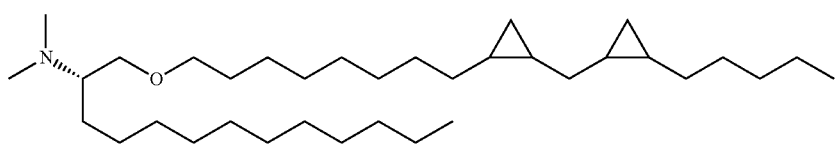

Compound xiv was carried on to final compound 19 as outlined for compound 1 above. LC/MS (M+H)=520.8.

Compound 20 is DLinKC2DMA as described in Nature Biotechnology, 2010, 28, 172-176, WO 2010/042877 A1, WO 2010/048536 A2, WO 2010/088537 A2, and WO 2009/127060 A1.

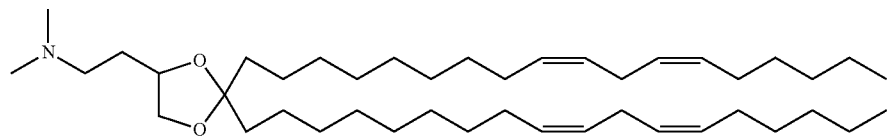

(20)

Compound 21 is MC3 as described in WO 2010/054401, and WO 2010/144740 A1.

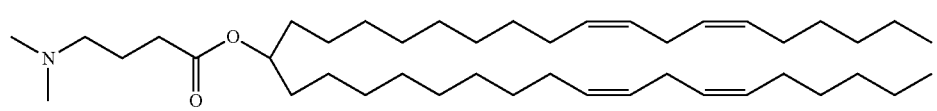

(21)

LNP Compositions

The following lipid nanoparticle compositions (LNPs) of the instant invention are useful for the delivery of oligonucleotides, specifically siRNA and miRNA:
Cationic Lipid/Cholesterol/PEG-DMG 56.6/38/5.4;
Cationic Lipid/Cholesterol/PEG-DMG 60/38/2;
Cationic Lipid/Cholesterol/PEG-DMG 67.3/29/3.7;
Cationic Lipid/Cholesterol/PEG-DMG 49.3/47/3.7;
Cationic Lipid/Cholesterol/PEG-DMG 50.3/44.3/5.4;
Cationic Lipid/Cholesterol/PEG-C-DMA/DSPC 40/48/2/10;
Cationic Lipid/Cholesterol/PEG-DMG/DSPC 40/48/2/10; and
Cationic Lipid/Cholesterol/PEG-DMG/DSPC 58/30/2/10.

LNP Process Description:

The Lipid Nano-Particles (LNP) are prepared by an impinging jet process. The particles are formed by mixing lipids dissolved in alcohol with siRNA dissolved in a citrate buffer. The mixing ratio of lipids to siRNA are targeted at 45-55% lipid and 65-45% siRNA. The lipid solution contains a novel cationic lipid of the instant invention, a helper lipid (cholesterol), PEG (e.g. PEG-C-DMA, PEG-DMG) lipid, and DSPC at a concentration of 5-15 mg/mL with a target of 9-12 mg/mL in an alcohol (for example ethanol). The ratio of the lipids has a mole percent range of 25-98 for the cationic lipid with a target of 35-65, the helper lipid has a mole percent range from 0-75 with a target of 30-50, the PEG lipid has a mole percent range from 1-15 with a target of 1-6, and the DSPC has a mole precent range of 0-15 with a target of 0-12. The siRNA solution contains one or more siRNA sequences at a concentration range from 0.3 to 1.0 mg/mL with a target of 0.3-0.9 mg/mL in a sodium citrate buffered salt solution with pH in the range of 3.5-5. The two liquids are heated to a temperature in the range of 15-40° C., targeting 30-40° C., and then mixed in an impinging jet mixer instantly forming the LNP. The teeID has a range from 0.25 to 1.0 mm and a total flow rate from 10-600 mL/min. The combination of flow rate and tubing ID has effect of controlling the particle size of the LNPs between 30 and 200 nm. The solution is then mixed with a buffered solution at a higher pH with a mixing ratio in the range of 1:1 to 1:3 vol:vol but targeting 1:2 vol:vol. This buffered solution is at a temperature in the range of 15-40° C., targeting 30-40° C. The mixed LNPs are held from 30 minutes to 2 hrs prior to an anion exchange filtration step. The temperature during incubating is in the range of 15-40° C., targeting 30-40° C. After incubating the solution is filtered through a 0.8 um filter containing an anion exchange separation step. This process uses tubing IDs ranging from 1 mm ID to 5 mm ID and a flow rate from 10 to 2000 mL/min. The LNPs are concentrated and diafiltered via an ultrafiltration process where the alcohol is removed and the citrate buffer is exchanged for the final buffer solution such as phosphate buffered saline. The ultrafiltration process uses a tangential flow filtration format (TFF). This process uses a membrane nominal molecular weight cutoff range from 30-500 KD. The membrane format can be hollow fiber or flat sheet cassette. The TFF processes with the proper molecular weight cutoff retains the LNP in the retentate and the filtrate or permeate contains the alcohol; citrate buffer; final buffer wastes. The TFF process is a multiple step process with an initial concentration to a siRNA concentration of 1-3 mg/mL. Following concentration, the LNPs solution is diafiltered against the final buffer for 10-20 volumes to remove the alcohol and perform buffer exchange. The material is then concentrated an additional 1-3 fold. The final steps of the LNP process are to sterile filter the concentrated LNP solution and vial the product.

Analytical Procedure:

1) siRNA Concentration

The siRNA duplex concentrations are determined by Strong Anion-Exchange High-Performance Liquid Chromatography (SAX-HPLC) using Waters 2695 Alliance system (Water Corporation, Milford Mass.) with a 2996 PDA detector. The LNPs, otherwise referred to as RNAi Delivery Vehicles (RDVs), are treated with 0.5% Triton X-100 to free total siRNA and analyzed by SAX separation using a Dionex BioLC DNAPac PA 200 (4×250 mm) column with UV detection at 254 nm. Mobile phase is composed of A: 25 mM $NaClO_4$, 10 mM Tris, 20% EtOH, pH 7.0 and B: 250 mM $NaClO_4$, 10 mM Tris, 20% EtOH, pH 7.0 with liner gradient from 0-15 min and flow rate of 1 ml/min. The siRNA amount is determined by comparing to the siRNA standard curve.

2) Encapsulation Rate

Fluorescence reagent SYBR Gold is employed for RNA quantitation to monitor the encapsulation rate of RDVs. RDVs with or without Triton X-100 are used to determine the free siRNA and total siRNA amount. The assay is performed using a SpectraMax M5e microplate spectrophotometer from Molecular Devices (Sunnyvale, Calif.). Samples are excited at 485 nm and fluorescence emission was measured at 530 nm. The siRNA amount is determined by comparing to the siRNA standard curve.

Encapsulation rate=(1-free siRNA/total siRNA)×100%

3) Particle Size and Polydispersity

RDVs containing 1 μg siRNA are diluted to a final volume of 3 ml with 1×PBS. The particle size and polydispersity of the samples is measured by a dynamic light scattering method using ZetaPALS instrument (Brookhaven Instruments Corporation, Holtsville, N.Y.). The scattered intensity is measured with He—Ne laser at 25° C. with a scattering angle of 90°.

4) Zeta Potential Analysis

RDVs containing 1 μg siRNA are diluted to a final volume of 2 ml with 1 mM Tris buffer (pH 7.4). Electrophoretic mobility of samples is determined using ZetaPALS instrument (Brookhaven Instruments Corporation, Holtsville, N.Y.) with electrode and He—Ne laser as a light source. The Smoluchowski limit is assumed in the calculation of zeta potentials.

5) Lipid Analysis

Individual lipid concentrations are determined by Reverse Phase High-Performance Liquid Chromatography (RP-HPLC) using Waters 2695 Alliance system (Water Corporation, Milford Mass.) with a Corona charged aerosol detector (CAD) (ESA Biosciences, Inc, Chelmsford, Mass.). Individual lipids in RDVs are analyzed using an Agilent Zorbax SB-C18 (50×4.6 mm, 1.8 μm particle size) column with CAD at 60° C. The mobile phase is composed of A: 0.1% TFA in H$_2$O and B: 0.1% TFA in IPA. The gradient changes from 60% mobile phase A and 40% mobile phase B from time 0 to 40% mobile phase A and 60% mobile phase B at 1.00 min; 40% mobile phase A and 60% mobile phase B from 1.00 to 5.00 min; 40% mobile phase A and 60% mobile phase 13 from 5.00 min to 25% mobile phase A and 75% mobile phase B at 10.00 min; 25% mobile phase A and 75% mobile phase 13 from 10.00 min to 5% mobile phase A and 95% mobile phase B at 15.00 min; and 5% mobile phase A and 95% mobile phase 13 from 15.00 to 60% mobile phase A and 40% mobile phase B at 20.00 min with flow rate of 1 ml/min. The individual lipid concentration is determined by comparing to the standard curve with all the lipid components in the RDVs with a quadratic curve fit. The molar percentage of each lipid is calculated based on its molecular weight.

Utilizing the above described LNP process, specific LNPs with the following ratios were identified:
Nominal Composition:
Cationic Lipid/Cholesterol/PEG-DMG 60/38/2
Cationic Lipid/Cholesterol/PEG-DMG/DSPC 58/30/2/10
Luc siRNA

```
                                          (SEQ. ID. NO.: 1)
5'-iB-AUAAGGCUAUGAAGAGAUATT-iB 3'
```

```
                                          (SEQ. ID. NO.: 2)
3'-UUUAUUCCGAUACUUCUCUAU-5'
AUGC - Ribose
iB - Inverted deoxy abasic
UC - 2' Fluoro
AGT - 2' Deoxy
AGU - 2' OCH_3
```

Nominal Composition
Cationic Lipid/Cholesterol/PEG-DMG 60/38/2
Cationic Lipid/Cholesterol/PEG-DMG/DSPC 40/48/2/10
Cationic Lipid/Cholesterol/PEG-DMG/DSPC 58/30/2/10
ApoB siRNA

```
                                          (SEQ ID NO.: 3)
5'-iB-CUUUAACAAUUCCUGAAAUTsT-iB-3'
```

```
                                          (SEQ ID NO.: 4)
3'-UsUGAAAUUGUUAAGGACUsUsUsA-5'
AUGC - Ribose
iB - Inverted deoxy abasic
UC - 2' Fluoro
AGT - 2' Deoxy
AGU - 2' OCH_3
UsA - phophorothioate linkage
```

Example 1

Mouse In Vivo Evaluation of Efficacy

LNPs utilizing Compounds 1-12, in the nominal compositions described immediately above, were evaluated for in vivo efficacy. The siRNA targets the mRNA transcript for the firefly (*Photinus pyralis*) luciferase gene (Accession # M15077). The primary sequence and chemical modification pattern of the luciferase siRNA is displayed above. The in vivo luciferase model employs a transgenic mouse in which the firefly luciferase coding sequence is present in all cells. ROSA26-LoxP-Stop-LoxP-Luc (LSL-Luc) transgenic mice licensed from the Dana Farber Cancer Institute are induced to express the Luciferase gene by first removing the LSL sequence with a recombinant Ad-Cre virus (Vector Biolabs). Due to the organo-tropic nature of the virus, expression is limited to the liver when delivered via tail vein injection. Luciferase expression levels in liver are quantitated by measuring light output, using an IVIS imager (Xenogen) following administration of the luciferin substrate (Caliper Life Sciences). Pre-dose luminescence levels are measured prior to administration of the RDVs. Luciferin in PBS (15 mg/mL) is intraperitoneally (IP) injected in a volume of 150 μL. After a four minute incubation period mice are anesthetized with isoflurane and placed in the IVIS imager. The RDVs (containing siRNA) in PBS vehicle were tail vein injected n a volume of 0.2 mL. Final dose levels ranged from 0.1 to 0.5 mg/kg siRNA. PBS vehicle alone was dosed as a control. Mice were imaged 48 hours post dose using the method described above. Changes in luciferin light output directly correlate with luciferase mRNA levels and represent an indirect measure of luciferase siRNA activity. In vivo efficacy results are expressed as % inhibition of luminescence relative to pre-dose luminescence levels. Systemic administration of the luciferase siRNA RDVs decreased luciferase expression in a dose dependant manner. Greater efficacy was observed in mice dosed with Compound 1 containing RDVs than with the RDV containing the octyl-CLinDMA (OCD) cationic lipid (FIG. 1). OCD is known and described in WO2010/021865.

Example 2

Rat In Vivo Evaluation of Efficacy and Toxicity

Figure 2:
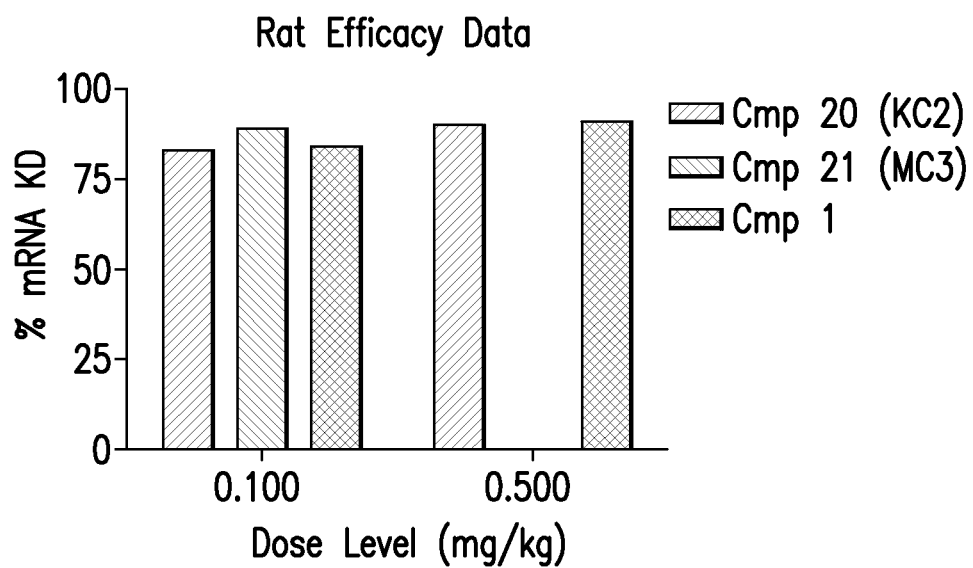
FIG. 2. LNP (Compound 1) efficacy in rat (ApoB siRNA).

LNPs utilizing compounds in the nominal compositions described above, were evaluated for in vivo efficacy and increases in alanine amino transferase and aspartate amino transferase in Sprague-Dawley (Crl:CD(SD) female rats (Charles River Labs). The siRNA targets the mRNA transcript for the ApoB gene (Accession # NM 019287). The primary sequence and chemical modification pattern of the ApoB siRNA is displayed above. The RDVs (containing siRNA) in PBS vehicle were tail vein injected in a volume of 1 to 1.5 mL. Infusion rate is approximately 3 ml/min. Five rats were used in each dosing group. After LNP administration, rats are placed in cages with normal diet and water present. Six hours post dose, food is removed from the cages. Animal necropsy is performed 24 hours after LNP dosing. Rats are anesthetized under isoflurane for 5 minutes, then maintained under anesthesia by placing them in nose cones continuing the delivery of isoflurane until exsanguination is completed. Blood is collected from the vena cava using a 23 gauge butterfly venipuncture set and aliquoted to serum separator vacutainers for serum chemistry analysis. Punches of the excised caudate liver lobe are taken and placed in RNALater (Ambion) for mRNA analysis. Preserved liver tissue was homogenized and total RNA isolated using a Qiagen bead mill and the Qiagen miRNA-Easy RNA isolation kit following the manufacturer's instructions. Liver ApoB mRNA levels were determined by quantitative RT-PCR. Message was amplified from purified RNA utilizing a rat ApoB commercial probe set (Applied Biosystems Cat # RN01499054_m1). The PCR reaction was performed on an ABI 7500 instrument with a 96-well Fast Block. The ApoB mRNA level is normalized to the housekeeping PPIB (NM 011149) mRNA. PPIB mRNA levels were determined by RT-PCR using a commercial probe set (Applied Biosytems Cat. No. Mm00478295_m1). Results are expressed as a ratio of ApoB mRNA/PPM mRNA. All mRNA data is expressed relative to the PBS control dose. Serum ALT and AST analysis were performed on the Siemens Advia 1800 Clinical Chemistry Analyzer utilizing the Siemens alanine aminotransferase (Cat#03039631) and aspartate aminotransferase (Cat#03039631) reagents. Similar efficacy was observed in rats dosed with Compound 1 containing RDV than with the RDV containing the cationic lipid DLinKC2DMA (Compound 20) or MC3 (Compound 21, FIG. 2). Additionally, 3 out of 4 rats treated with 3 mg/kg DLinKC2DMA (Compound 20) failed to survive 48 hours and 2 out of 4 rats treated with 3 mg/kg MC3 (Compound 21) failed to survive 48 hours. 1 out of 4 rats treated with 10 mg/kg Compound 1 survived at 48 hours post dose.

Example 3

Determination of Cationic Lipid Levels in Rat Liver

Liver Tissue was Weighed into 20-ml Vials and Homogenized in 9 v/w of Water using a GenoGrinder 2000 (OPS Diagnostics, 1600 strokes/min, 5 min). A 50 µL aliquot of each tissue homogenate was mixed with 300 µL of extraction/protein precipitating solvent (50/50 acetonitrile/methanol containing 500 nM internal standard) and the plate was centrifuged to sediment precipitated protein. A volume of 200 µL of each supernatant was then transferred to separate wells of a 96-well plate and 10 µl samples were directly analyzed by LC/MS-MS.

Standards were prepared by spiking known amounts of a methanol stock solution of ompound into untreated rat liver homogenate (9 vol water/weight liver). Aliquots (50 µL) each standard/liver homogenate was mixed with 300 µL of extraction/protein precipitating solvent (50/50 acetonitrile/methanol containing 500 nM internal standard) and the plate was centrifuged to sediment precipitated protein. A volume of 200 µL of each supernatant was transferred to separate wells of a 96-well plate and 10 µl of each standard was directly analyzed by LC/MS-MS.

Absolute quantification versus standards prepared and extracted from liver homogenate was performed using an Aria LX-2HPLC system (Thermo Scientific) coupled to an API 4000 triple quadrupole mass spectrometer (Applied Biosystems). For each run, a total of 10 µL sample was injected onto a BDS Hypersil CS HPLC column (Thermo, 50×2 mm, 3 µm) at ambient temperature.

Figure 3:
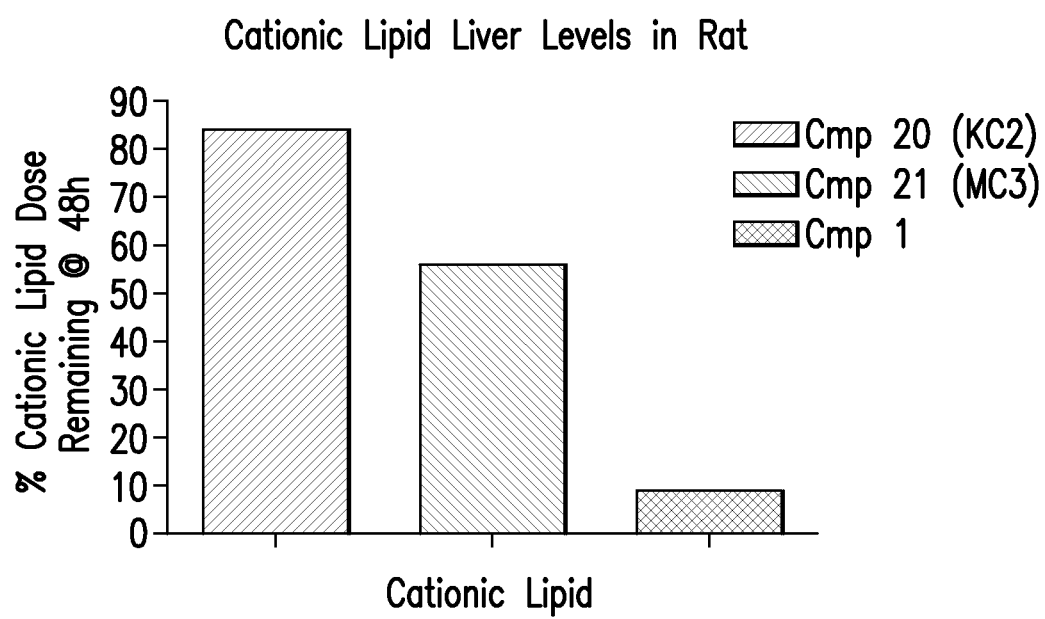
FIG. 3. Cationic lipid (Compound 1) levels in rat liver.

Mobile Phase A: 95% $H_2O$/5% methanol/10 mM ammonium formate/0.1% formic acid Mobile Phase B: 40% methanol/60% n-propanol/10 mM ammonium formate/0.1% formic acid The flow rate was 0.5 mL/min and gradient elution profile was as follows: hold at 80% A for 0.25 min, linear ramp to 100% B over 1.6 min, hold at 100% B for 2.5 min, then return and hold at 80% A for 1.75 min. Total run time was 5.8 min. API 4000 source parameters were CAD: 4, CUR: 15, GS1: 65, GS2: 35, IS: 4000, TEM: 550, CXP: 15, DP: 60, EP: 10. In rats dosed with Compound 1 containing RDV liver levels were lower than with the RDV containing the cationic lipid DLinKC2DMA (Compound 20) or MC3 (Compound 21, FIG. 3).

What is claimed is:

1. A cationic lipid of Formula A:

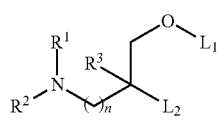

wherein:

$R^1$ and $R^2$ are independently selected from H, ($C_1$-$C_6$) alkyl, heterocyclyl, and polyamine, wherein said alkyl, heterocyclyl and polyamine are optionally substituted with one to three substituents selected from R', or $R^1$ and $R^2$ can be taken together with the nitrogen to which they are attached to form a monocyclic heterocycle with 4-7 members optionally containing, in addition to the nitrogen, one or two additional heteroatoms selected from N, O and S, said monocyclic heterocycle is optionally substituted with one to three substituents selected from R';

$R^3$ is selected from H and ($C_1$-$C_6$)alkyl, said alkyl optionally substituted with one to three substituents selected from R';

R' is independently selected from halogen, R", OR", SR", CN, $CO_2$R" and CON(R")$_2$;

R" is independently selected from H and ($C_1$-$C_6$)alkyl, wherein said alkyl is optionally substituted with halogen and OH;

n is 0, 1, 2, 3, 4 or 5; and $L_1$ is $C_{12}$-$C_{24}$ alkenyl, said alkenyl are optionally substituted with one or more substituents selected from R;

$L_2$ is selected from $C_3$-$C_{24}$ alkyl and $C_3$-$C_{24}$ alkenyl, said alkyl and alkenyl are optionally substituted with one or more substituents selected from R';

or any pharmaceutically acceptable salt or stereoisomer thereof.

2. A cationic lipid of Formula A according to claim 1, wherein:

$R^1$ and $R^2$ are each methyl;

$R^3$ is H;

n is 0;

$L_1$ is $C_{12}$-$C_{24}$ alkenyl; and $L_2$ is selected from $C_5$-$C_9$ alkyl and $C_5$-$C_9$ alkenyl;

or any pharmaceutically acceptable salt or stereoisomer thereof.

3. A cationic lipid of Formula A according to claim 1, wherein:

$R^1$ and $R^2$ are each methyl;

$R^3$ is H;

n is 1;

$L_1$ is $C_3$-$C_{24}$ alkenyl; and $L_2$ is selected from $C_5$-$C_9$ alkyl and $C_5$-$C_9$ alkenyl;

or any pharmaceutically acceptable salt or stereoisomer thereof.

4. A cationic lipid of Formula A: according to claim 1

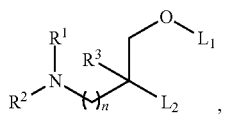

wherein:
R$^1$ and R$^2$ are each methyl;
R$^3$ is H;
n is 2;
L$_1$ is selected from C$_3$-C$_{24}$ alkyl and C$_3$-C$_{24}$ alkenyl; and
L$_2$ is selected from C$_5$-C$_9$ alkyl and C$_5$-C$_9$ alkenyl;
or any pharmaceutically acceptable salt or stereoisomer thereof.

5. A cationic lipid which is selected from:
(2S)—N,N-dimethyl-1-[(9Z,12Z)-octadeca-9,12-dien-1-yloxy]undecan-2-amine (Compound 1);
(2S)-1-[(9Z,12Z)-octadeca-9,12-dien-1-yloxy]undecan-2-amine (Compound 2);
(2S)-1-[(9Z,12Z)-octadeca-9,12-dien-1-yloxy]dodecan-2-amine (Compound 3);
(2S)-1-[(9Z,12Z)-octadeca-9,12-dien-1-yloxy]dodecan-2-amine (Compound 4);
(2S)-1-[(9Z,12Z)-octadeca-9,12-dien-1-yloxy]decan-2-amine (Compound 5);
(2S)-1-[(9Z,12Z)-octadeca-9,12-dien-1-yloxy]nonan-2-amine (Compound 6);
(2S)—N,N-dimethyl-1-[(9Z,12Z)-octadeca-9,12-dien-1-yloxy]tridecan-2-amine (Compound 7);
(2S)—N,N-dimethyl-1-[(9Z,12Z)-octadeca-9,12-dien-1-yloxy]nonan-2-amine (Compound 8);
(2S)—N,N-dimethyl-1-[(9Z,12Z)-octadeca-9,12-dien-1-yloxy]dodecan-2-amine (Compound 9);
(2S)—N,N-dimethyl-1-[(9Z,12Z)-octadeca-9,12-dien-1-yloxy]dodecan-2-amine (Compound 10);
(2S)—N,N-dimethyl-1-[(9Z,12Z)-octadeca-9,12-dien-1-yloxy]decan-2-amine (Compound 11); and
(2S,12Z,15Z)—N,N-dimethyl-1-(octyloxy)henicosa-12,15-dien-2-amine (Compound 12);
(2S,12Z,15Z)-1-(decyloxy)-N,N-dimethylhenicosa-12,15-dien-2-amine (Compound 13);
(2S,12Z,15Z)-1-(hexyloxy)-N,N-dimethylhenicosa-12,15-dien-2-amine (Compound 14);
(2S,12Z,15Z)-1-(hexadecyloxy)-N,N-dimethylhenicosa-12,15-dien-2-amine (Compound 15);
(2S,12Z,15Z)—N,N-dimethyl-1-(undecyloxy)henicosa-12,15-dien-2-amine (Compound 16);
N,N-dimethyl-2{-[(9Z,12Z)-octadeca-9,12-dien-1-yloxy]methyl}undecan-1-amine (Compound 17);
N,N-dimethyl-3-{[(9Z,12Z)-octadeca-9,12-digin-1-yloxy]methyl}dodecan-1-amine (Compound 18); and
(2S)—N,N-dimethyl-1-({8-[(1R,2R)-2-{[(1S,2S)-2-pentylcyclopropyl]methyl}cyclopropyl]octyl}oxy)tridecan-2-amine (Compound 19);

or any pharmaceutically acceptable salt or stereoisomer thereof.

6. A lipid nanoparticle comprising a cationic lipid according to claim 1.

7. The lipid nanoparticle according to claim 6, wherein the lipid nanoparticle further comprises an oligonucleotide.

8. The lipid nanoparticle according to claim 7, wherein the oligonucleotide is siRNA or miRNA.

9. The lipid nanoparticle according to claim 8 wherein the oligonucleotide is siRNA.

10. A cationic lipid of Formula A:

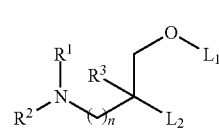

wherein:
R$^1$ and R$^2$ are independently selected from H, (C$_1$-C$_6$) alkyl, heterocyclyl, and polyamine, wherein said alkyl, heterocyclyl and polyamine are optionally substituted with one to three substituents selected from R', or R$^1$ and R$^2$ can be taken together with the nitrogen to which they are attached to form a monocyclic heterocycle with 4-7 members optionally containing, in addition to the nitrogen, one or two additional heteroatoms selected from N, O and S, said monocyclic heterocycle is optionally substituted with one to three substituents selected from R';
R$^3$ is selected from H and (C$_1$-C$_6$)alkyl, said alkyl optionally substituted with one to three substituents selected from R';
R' is independently selected from halogen, R", OR", SR", CN, CO$_2$R" and CON(R")$_2$;
R" is independently selected from H and (C$_1$-C$_6$)alkyl, wherein said alkyl is optionally substituted with halogen and OH;
n is 0, 1, 2, 3, 4 or 5; and
L$_1$ is selected from C$_3$-C$_{24}$ alkyl and C$_3$-C$_{24}$ alkenyl, said alkyl and alkenyl are optionally substituted with one or more substituents selected from R';
L$_2$ is C$_{12}$-C$_{24}$ alkenyl, which is optionally substituted;
or any pharmaceutically acceptable salt or stereoisomer thereof.

11. A cationic lipid of Formula A according to claim 10, wherein:
R$^1$ and R$^2$ are each methyl;
R$^3$ is H;
n is 0;
L$_1$ is selected from C$_3$-C$_9$ alkyl and C$_3$-C$_9$ alkenyl; and
L$_2$ is C$_{12}$-C$_{24}$ alkenyl;
or any pharmaceutically acceptable salt or stereoisomer thereof.

* * * * *